(12) United States Patent
Patterson et al.

(10) Patent No.: US 8,721,694 B2
(45) Date of Patent: May 13, 2014

(54) BONE SCREW WASHER

(75) Inventors: Chad J. Patterson, Shady Mill Cove, TN (US); Gary W. Lowery, Eads, TN (US); Vernon R. Hartdegen, Collierville, TN (US)

(73) Assignee: Wright Medical Technology, Inc., Memphis, TN (US)

( * ) Notice: Subject to any disclaimer, the term of this patent is extended or adjusted under 35 U.S.C. 154(b) by 1264 days.

(21) Appl. No.: 11/759,579

(22) Filed: Jun. 7, 2007

(65) Prior Publication Data
US 2008/0306555 A1 Dec. 11, 2008

(51) Int. Cl.
*A61B 17/84* (2006.01)

(52) U.S. Cl.
USPC .......................................... 606/300

(58) Field of Classification Search
USPC ............... 606/69, 73, 91, 104, 289, 290, 291, 606/300, 301, 315, 60, 65, 72, 302, 303, 606/319; 411/399, 531, 396, 480, 533, 537, 411/538, 541, 542, 546; 285/98, 110, 113, 285/339, 342, 343, 349, 386, 388, 389; 277/403
See application file for complete search history.

(56) References Cited

U.S. PATENT DOCUMENTS

| | | | |
|---|---|---|---|
| 1,031,368 A * | 7/1912 | Perry | 52/543 |
| 2,280,183 A * | 4/1942 | Bennett | 277/605 |
| 2,537,575 A * | 1/1951 | Crowther | 411/134 |
| 3,788,185 A * | 1/1974 | Gutshall | 411/371.1 |
| RE33,348 E | 9/1990 | Lower | |
| 4,988,351 A | 1/1991 | Paulos et al. | |
| 5,084,050 A | 1/1992 | Draenert | |
| 5,098,434 A | 3/1992 | Serbousek | |
| 5,100,274 A * | 3/1992 | Hasan et al. | 411/368 |
| 5,409,486 A * | 4/1995 | Reese | 606/916 |
| 5,643,265 A * | 7/1997 | Errico et al. | 606/70 |
| 5,666,745 A * | 9/1997 | Harwood | 36/77 R |
| 5,899,906 A | 5/1999 | Schenk | |
| 5,915,903 A * | 6/1999 | Osterle et al. | 411/531 |
| 5,954,722 A * | 9/1999 | Bono | 606/281 |
| 5,976,141 A * | 11/1999 | Haag et al. | 606/292 |
| 5,997,541 A | 12/1999 | Schenk | |
| 6,039,525 A * | 3/2000 | Johnson | 411/353 |
| 6,048,344 A * | 4/2000 | Schenk | 606/916 |
| 6,214,007 B1 * | 4/2001 | Anderson | 606/304 |
| 6,241,731 B1 * | 6/2001 | Fiz | 606/65 |
| 2005/0033298 A1 * | 2/2005 | Hawkes et al. | 606/61 |
| 2005/0240190 A1 * | 10/2005 | Gall et al. | 606/72 |
| 2006/0195103 A1 * | 8/2006 | Padget et al. | 606/72 |

FOREIGN PATENT DOCUMENTS

| | | | | |
|---|---|---|---|---|
| WO | WO 97/25930 | * | 2/1997 | A61B 17/68 |
| WO | WO 2007/014192 | * | 2/2007 | A61B 17/80 |

* cited by examiner

*Primary Examiner* — Christian Sevilla
(74) *Attorney, Agent, or Firm* — Duane Morris LLP

(57) ABSTRACT

A washer for use with a bone screw in the reduction and fixation of bone fragments includes a frusto-conical body having a leading end, a trailing end, an exterior surface and an interior surface. A central bore defined by the interior surface for insertion of a bone screw extends longitudinally through the washer. The interior surface is tapered resulting in the central bore's diameter being larger at the trailing end than at the leading end. The washer, when used in combination with a compression bone screw, improves seating of the bone screw head in the bone and results in enhanced compression.

10 Claims, 7 Drawing Sheets

BONE SCREW WASHER

FIELD OF THE INVENTION

The present invention relates generally to a washer for use with a bone screw.

BACKGROUND

Compression bone screws are often used in the treatment of nonunion and fracture of bone fragments, generally two bone fragments. Some compression bone screws have two threaded portions, a threaded distal end for engaging the first of the two bone fragments and a threaded proximal end for engaging the second of the two bone fragments. The two threaded ends of such compression bone screw are designed to generate compression force and bring the two bone fragments together.

Sometimes, the bone fragment at the proximal end of the bone screw may not have the sufficient structural integrity for the threaded proximal end of the bone screw to threadably engage the bone. Or the bone screw may have initially threadably engaged to the proximal bone fragment but the threads in the bone was stripped, and thus the screw is unable to properly engage the bone fragment. In these types of situations, the existing bone fixations systems do not provide optimal solutions for joining and fixating the bone fragments. Therefore, an improved bone fixation system is needed.

SUMMARY

According to an embodiment, a washer for use with a bone screw in the reduction and fixation of bone fragments is disclosed. The washer has a frusto-conical body having a leading end, a trailing end, an exterior surface and an interior surface. A central bore, extending longitudinally through the washer, is formed by the interior surface for insertion of the bone screw. The interior surface is tapered such that the central bore's diameter is largest at the trailing end. The leading end of the washer also includes an inwardly extending flange that further reduces the diameter of the central bore at the leading end to be smaller than the head or the proximal end of the particular bone screw being used in combination with the washer such that the flange and the head of the bone screw engage each other preventing the head of the bone screw from passing completely through the washer. The washer's length along its longitudinal (or central) axis is sufficiently long such that the central bore is deep enough to countersink the bone screw's head or the proximal end.

According to another embodiment, a bone fixation system including one or more of the washer described above and one or more bone screws for using in combination with the one or more washers is disclosed.

The washer provides the ability to use a compression bone screw when the proximal bone fragment is structurally compromised to properly engage the threaded proximal portion of the compression bone screw. According to another embodiment, the washer can be used with a bone screw with a non-threaded head.

BRIEF DESCRIPTION OF THE DRAWINGS

The features shown in the above referenced drawings are illustrated schematically and are not intended to be drawn to scale nor are they intended to be shown in precise positional relationship. Like reference numbers indicate like elements.

DETAILED DESCRIPTION

Figure 1:
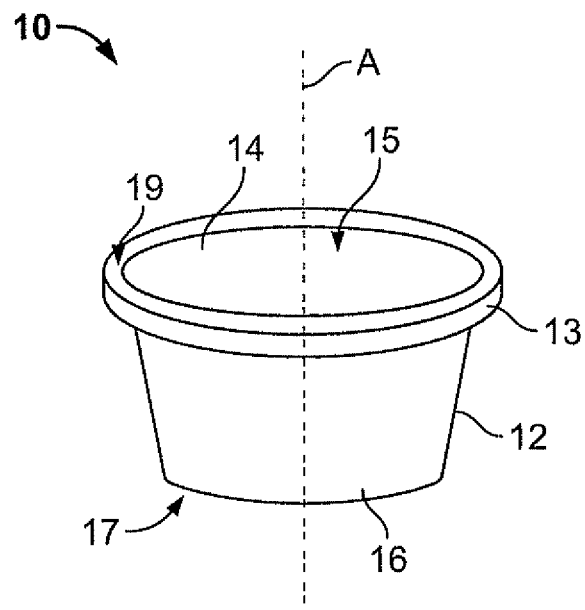
FIG. 1 is a perspective view of a washer according to an embodiment.
Figure 2:
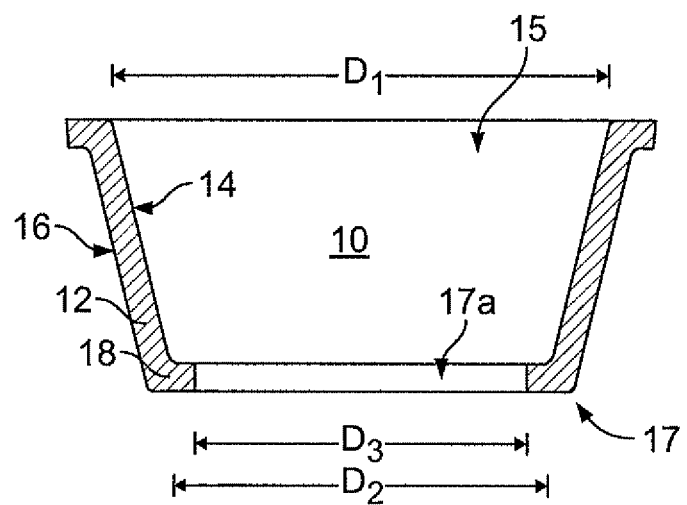
FIG. 2 is a cross-sectional view of the washer embodiment of FIG. 1.

In the following detailed description of the preferred embodiments, reference is made to the accompanying drawings which form a part hereof, and in which are shown by way of illustration specific embodiments in which the invention may be practiced. It is to be understood that other embodiments may be utilized and structural changes may be made without departing from the scope of the present invention.

Referring to FIGS. 1-5, a washer 10 according to an embodiment is disclosed. The washer 10's structural configuration is optimal for straight or perpendicular approaches with respect to the surface of the bone into which the washer is embedded to allow seating of the proximal end of a compression bone screw. The washer 10 comprises a frusto-conical body 12 having a leading end 17 and a trailing end 19. The terms "leading" and "trailing" referring to the direction the washer is pressed or pushed into a bone fragment in actual use. The frusto-conical body 12 has a tapered external surface 16 and an internal surface 14. A central bore 15 extending along a central axis A of the washer is defined by the interior surface 14. The frusto-conical body 12 increases in diameter from leading end 17 to the trailing end 19. The interior surface 14 is tapered, generally following the contour of the frusto-conical body 12 and, thus, the diameter of the central bore 15 has its largest diameter D1 at the trailing end 19 and smallest diameter D2 near the leading end 17. The interior surface 14 is tapered at an angle α of about 4 to 8° with respect to the central axis A. In a preferred embodiment, the angle α is about 6°. In the illustrated embodiment, the exterior surface 16 has a taper angle β that is at least the same as the angle α.

At the leading end 17, a flange 18 extends inwardly forming an opening 17a having a diameter D3 that is smaller than the diameter D2, thus, further restricting the central bore at the leading end 17. A trailing end flange 13 extends outwardly at the trailing end 19.

Figure 3:
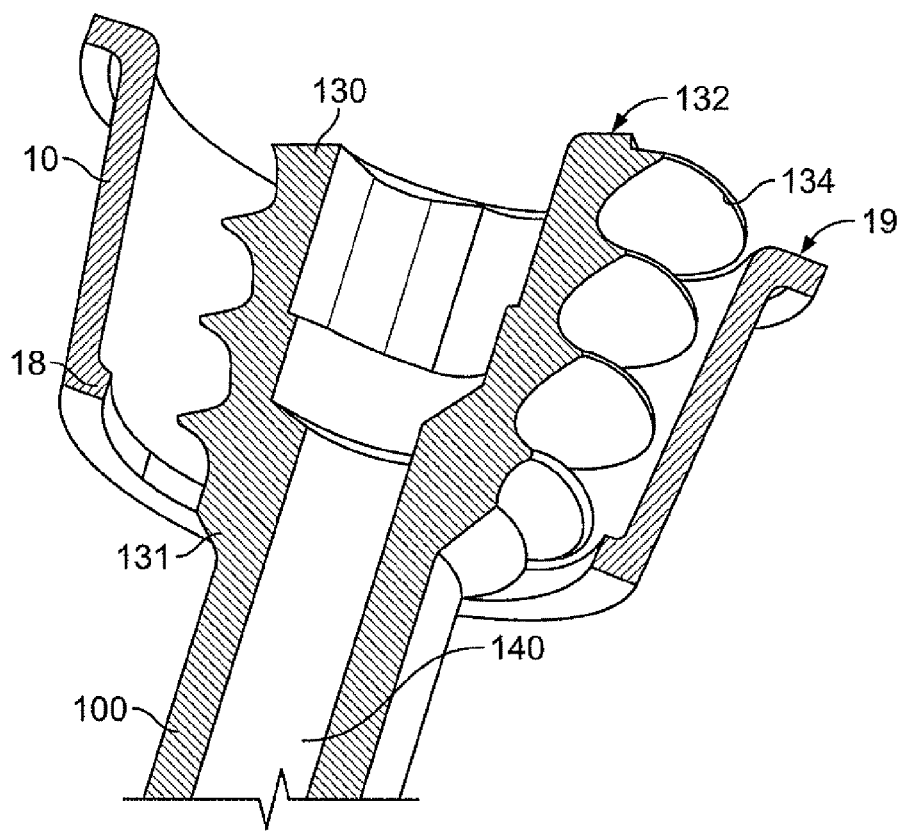
FIG. 3 is a perspective cross-sectional view of the washer embodiment of FIG. 1 shown in combination with a compression bone screw having a threaded proximal portion according to another embodiment.
Figure 4:
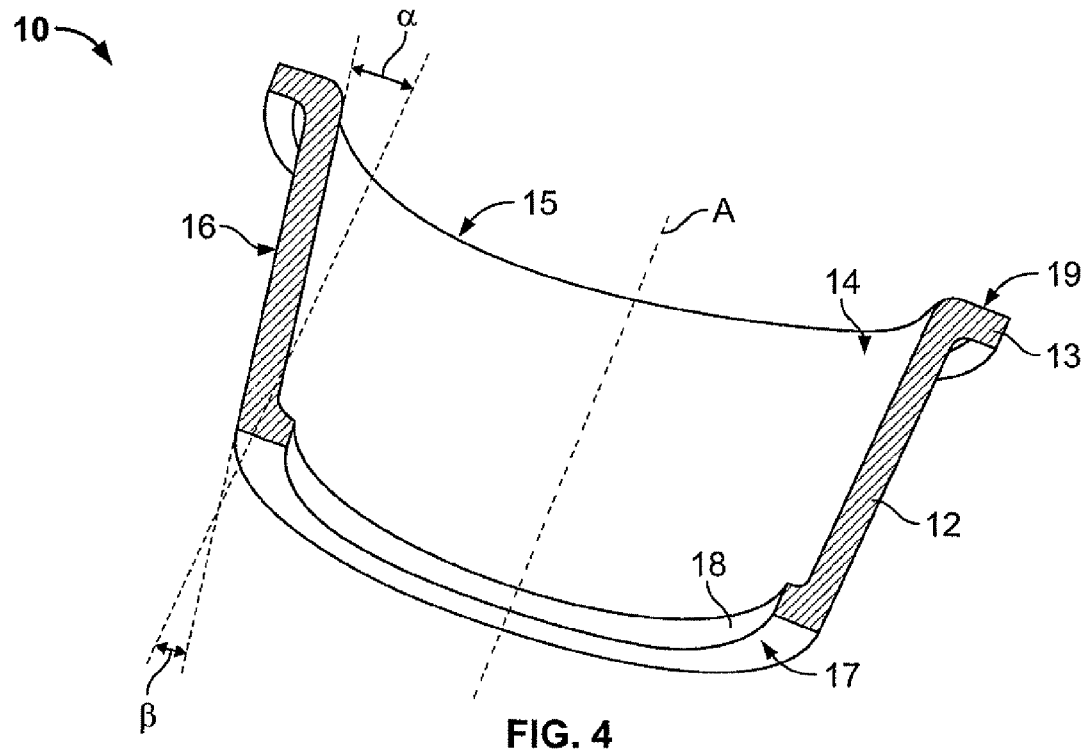
FIG. 4 is a perspective cross-sectional view of the washer embodiment of FIG. 1.
Figure 12:
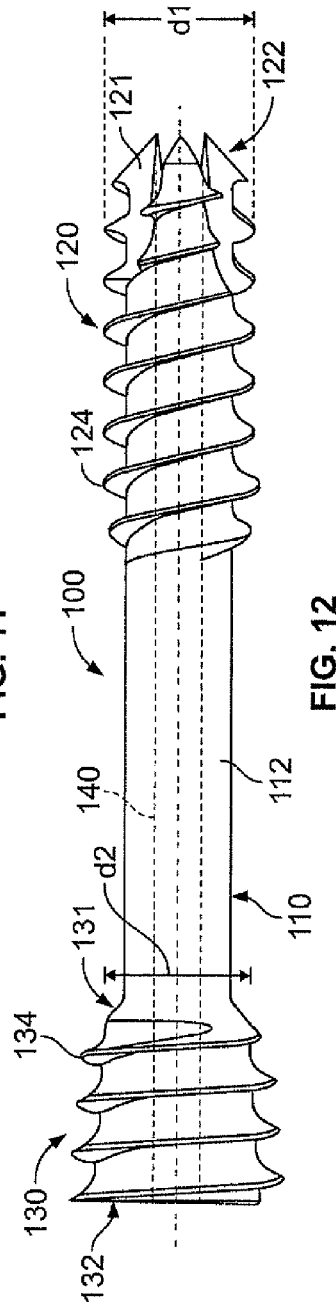
FIG. 12 is a plan view of an example of a bone screw that can be used in combination with the washers described herein.

FIG. 3 shows the washer 10 in combination with a bone screw 100 having a threaded proximal portion 130. The exemplary details of the bone screw 100 that can be used in combination with the washer 10 is shown in FIG. 12 and the structure of such bone screw 100 is further described below with farther references to FIG. 12. In actual use, the washer 10 would be inserted into the structurally compromised proximal bone fragment with its leading end 17 first. At this point, the trailing end 19 of the washer may or may not be flush with the surface of the proximal bone fragment. A bone screw is then inserted into the central bore 15 of the washer so that the distal threaded end of the bone screw passes through the washer, through the proximal bone fragment, and threadably engages a distally located bone fragment. As the bone screw threadably engages, the proximal end of the bone screw countersinks into the central bore 15 of the washer and pushes the washer against the proximal bone fragment and generates the compression force necessary to join the two bone fragments together. The structural relationship between the proximal end of the bone screw and the washer 10 is described in more detail below.

In some bone screws, the proximal portion 130 can be tapered so that the major diameter of the proximal thread 134 at the proximal end 132 is larger than the major diameter of the proximal thread 134 at the distal end 131. In other bone screws, the proximal portion 130 may be straight. In either case, the major diameter of the proximal thread 134 at the distal end 131 of the proximal portion 130 is larger than the diameter D3 of the leading end opening 17a of the washer 10 preventing the proximal portion 130 to go through the leading end opening 17a. This interference allows the proximal portion 130 to engage the washer 10 and push against the washer as the bone screw is advanced into the bone and generates compression between the bone fragments being joined with does not go through the washer. The diameter of the tapered central bore 15 is sufficiently large to accommodate the proximal portion 130 of the bone screw whether the proximal portion 130 is tapered or straight.

Thus, as the distal threads 124 (see FIG. 12) of the bone screw 100 engages the distal bone fragment, the interference between the proximal thread 134 and the flange 18 of the washer 10 enables the proximal portion 130 of the bone screw to push the washer 10 against and into the proximal bone fragment and maintain the trailing end 19 to be substantially flush with the surface of the bone when the trailing end flange 13 stops against the surface of the bone.

The washer 10 is an embodiment that is optimally suited for using in combination with a bone screw for immobilizing bone fragments where the bone screw's approach to the bone surface is perpendicular as in calcaneal displacement osteotomies, for example. The central axis A of the washer 10 should align with the longitudinal axis of the bone screw and, thus, the washer 10 would be inserted into the bone straight allowing the trailing end 19 of the washer 10 to be flush with the surface of the bone. This will allow the proximal end of the bone screw to countersink into the central bore 15 of the washer 10.

Figure 5:
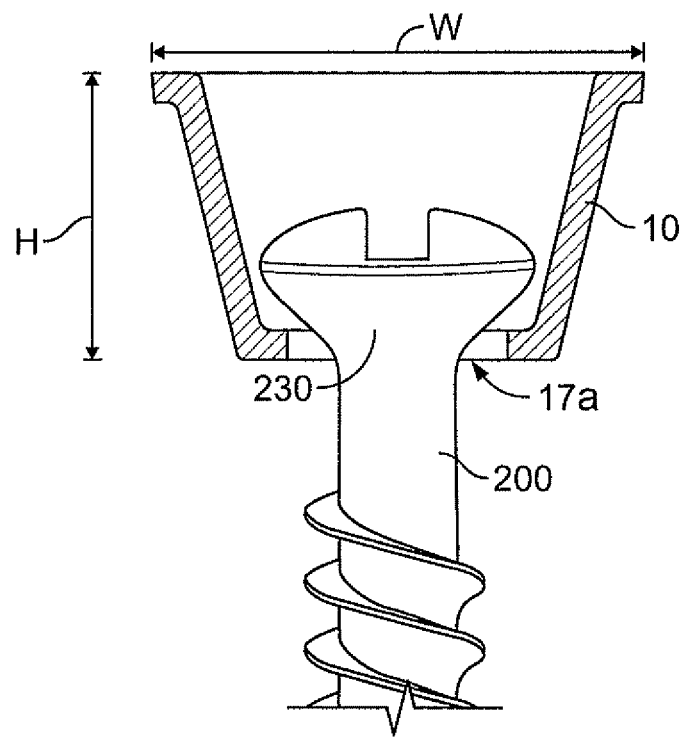
FIG. 5 is a cross-sectional view of the washer embodiment of FIG. 1 shown in combination with a bone screw having a conventional non-threaded head.
Figure 6:
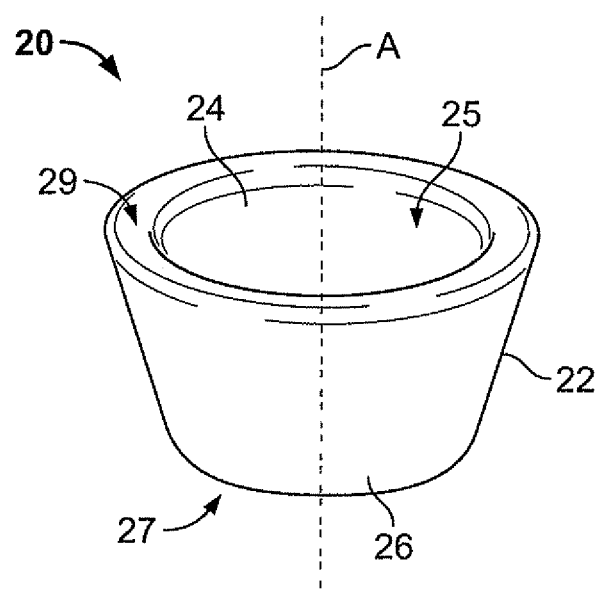
FIG. 6 is a perspective view of a washer according to another embodiment.

FIG. 5 shows the washer 10 in combination with another example of a bone screw 200. The bone screw 200 has a non-threaded screw head 230. The screw head 230 is larger in diameter than the leading end opening 17a of the washer. Thus, similar to the way the bone screw 100 engaged the washer 10, as the screw 200 is threadably engaged with a distally located bone fragment and advances into the bone, the screw head 230 pushes the washer 10 into the proximal bone fragment until the washer 10 is seated in the bone.

Referring to FIGS. 6-10, a washer 20 according to another embodiment is described. The washer 20's structural configuration is optimal for oblique approaches with respect to the surface of the bone into which the washer is embedded. The washer 20 comprises a frusto-conical body 22 having a leading end 27 and a trailing end 29. The frusto-conical body 22 has a tapered external surface 26 and an internal surface 24. A central bore 25 extending along a central axis A of the washer is defined by the interior surface 24. The frusto-conical body 22 increases in diameter from leading end 27 to the trailing end 29.

Figure 9:
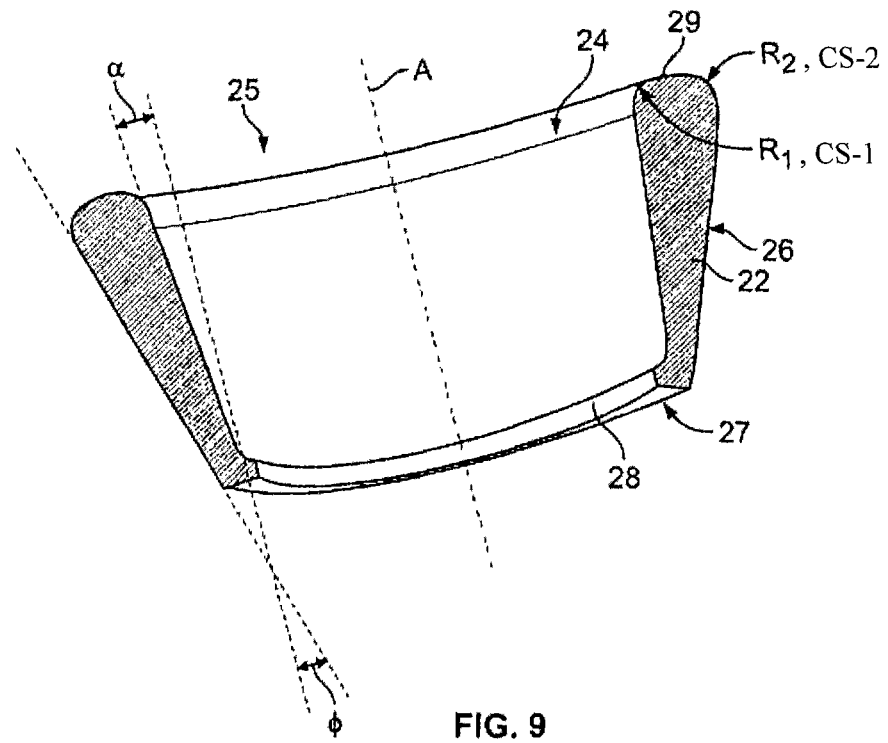
FIG. 9 is a perspective cross-sectional view of the washer embodiment of FIG. 6.

As shown in FIG. 9, unlike in the washer 10 of the first embodiment, the internal surface 24 is tapered at an angle α with respect to the central axis A and the external surface 26 is tapered at an angle Ø that is greater than the taper angle α of the internal surface 24. This gives the washer 20 a cross-sectional segment shape that is wedge-like with the thicker end at the trailing end 29 of the washer 20. The angle α can be about 4 to 8° and preferably about 6°. The angle Ø is about 15 to 25° and preferably about 20°. The trailing end 29 of the washer 20 has a curved surface that connects the internal surface 24 to the external surface 26. Thus, the washer 20 of this embodiment projects smooth, minimally obtrusive, protrusion on the surface of the proximal bone fragment when the washer 20 and the associated bone screw approaches the proximal bone fragment at an oblique angle. The larger taper-angled external surface 26 of the washer 20 prevents the washer 20 from embedding into the bone too much and helps transfer and distribute the compressive force of the advancing bone screw to the proximal bone fragment.

As with the washer 10 of the first embodiment, the diameter of the central bore 25 has its largest diameter D1 at the trailing end 29 and smallest diameter D2 near the leading end 27. At the leading end 27, a flange 28 extends inwardly forming an opening 27a having a diameter D3 that is smaller than the diameter D2, thus, further restricting the central bore at the leading end 27. A trailing end flange 23 extends outwardly at the trailing end 29.

Figure 8:
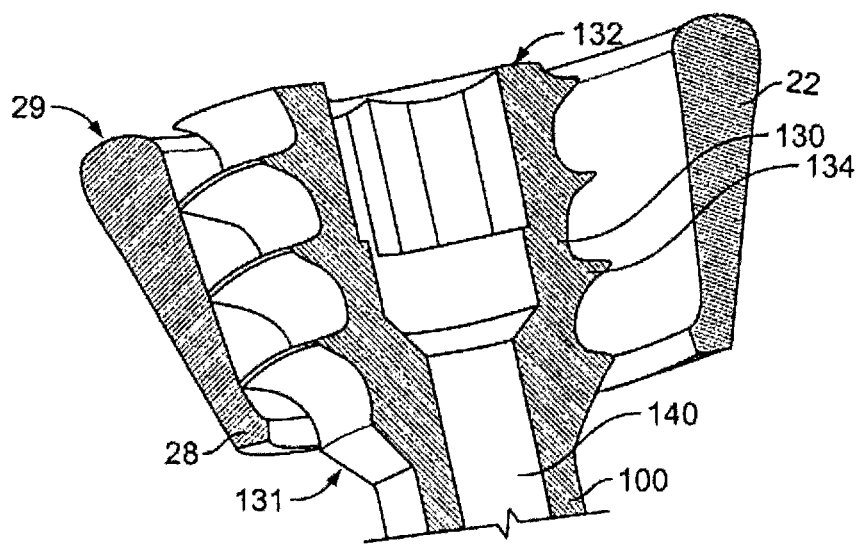
FIG. 8 is a perspective cross-sectional view of the washer embodiment of FIG. 6 shown in combination with a compression bone screw having a threaded proximal portion according to another embodiment.

FIG. 8 shows the washer 20 in combination with a bone screw 100 having a threaded proximal portion 230. The exemplary details of the bone screw 100 that can be used in combination with the washer 20 is shown in FIG. 12 and the structure of such bone screw 100 is further described below with further references to FIG. 12. In actual use, the washer 20 would be inserted into the structurally compromised proximal bone fragment with its leading end 27 first. At this point, the trailing end 29 of the washer may or may not be flush with the surface of the proximal bone fragment. A bone screw is then inserted into the central bore 25 of the washer so that the distal threaded end of the bone screw passes through the washer, through the proximal bone fragment, and threadably engages a distally located bone fragment. As the bone screw threadably engages, the proximal end of the bone screw countersinks into the central bore 25 of the washer and pushes the washer against the proximal bone fragment and generates the compression force necessary to join the two bone fragments together. The structural relationship between the proximal end of the bone screw and the washer 20 is described in more detail below.

Figure 7:
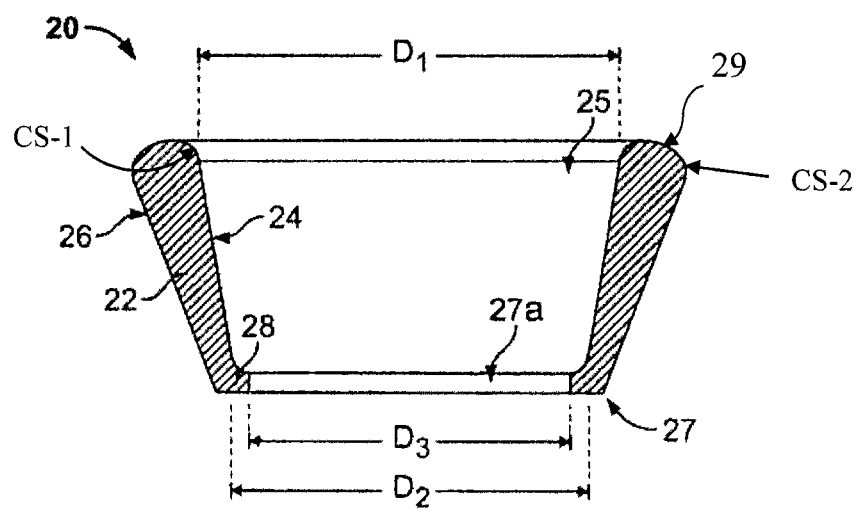
FIG. 7 is a cross-sectional view of the washer embodiment of FIG. 6.

As shown in FIG. 7, the various diameters associated with the central bore 25 of the washer 20 is configured similar to the washer 10 of the first embodiment and, thus, the washer 20's tapered central bore 25 can accommodate a bone screw 100 having tapered as well as non-tapered proximal portion 130. In other words, the major diameter of the proximal thread 134 at the distal end 131 of the proximal portion 130 is larger than the diameter D3 of the leading end opening 27a of the washer 20 preventing the proximal portion 130 to go through the leading end opening 27a. This interference allows the proximal portion 130 to engage the washer 20 and push against the washer as the bone screw is advanced into the bone and generates compression between the bone fragments being joined with does not go through the washer. The diameter of the tapered central bore 25 is sufficiently large to accommodate the proximal portion 130 of the bone screw whether the proximal portion 130 is tapered or straight.

Thus, as the distal threads 124 (see FIG. 12) of the bone screw 100 engages the distal bone fragment, the interference between the proximal thread 134 and the flange 28 of the washer 20 enables the proximal portion 130 of the bone screw to push the washer 20 against and into the proximal bone fragment. Because the washer 20 is generally intended for use in oblique approach angle to the bone the trailing end 29 of the washer 20 comprises a curved surface that connects the internal surface 24 to the external surface 26.

As shown in FIGS. 7 and 9, the first curved surface CS-1 between the internal surface 24 and the trailing end 29 has a radius of curvature R1. The second curved surface CS-2 between the external surface 26 and the trailing end 29 has a radius of curvature R2. Because the washer 20 is intended for use in applications where the bone screw's approach, and thus the washer 20's approach is oblique to the bone surface, the washer 20 is generally not flush with the surface of the bone. In other words, a portion of the trailing end 29 will generally be protruding out from the surface of the bone. But the curved surface defined by the radius of curvature R2 at the trailing end 29 of the washer 20 provides a smooth surface for the protrusion and minimize any soft tissue damage. Such washer 20 is useful for applications such as ankle fusions or other angled approaches. The radius of curvature R1 is at least about $50/1000$ inches and the radius of curvature R2 is at least about $20/1000$ inches.

Figure 11:
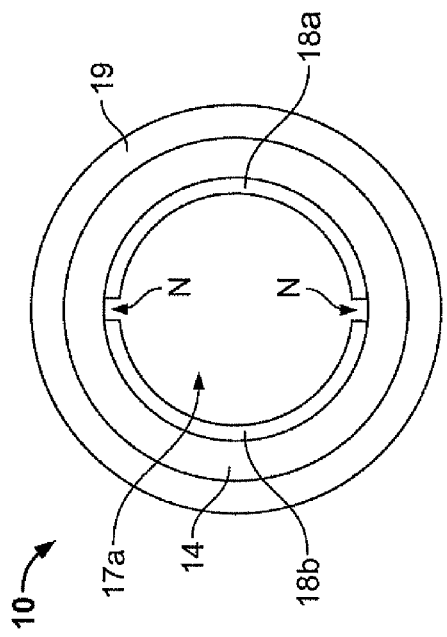
FIG. 11 is a bottom view of an embodiment of the washer.

According to another embodiment, the flanges 18, 28 at the leading ends 17, 27 of the washers 10, 20, respectively, can be provided in two or more segments. For example, FIG. 11 shows a view from the top or trailing end 19 of the washer 10 where the flange 18 segmented in two segments 18a and 18b by notches N.

FIG. 12 is an illustration of one example of a bone screw 100 having a threaded proximal portion 130 that can be used in combination with the washer embodiments described herein. The bone screw 100 comprises a shaft 112, a proximal portion 130 and a distal portion 120. The proximal portion 130 has a proximal screw thread 134 provided thereon extending from the distal end 131 of the proximal portion 130 to the proximal end 132 of the proximal portion 130. The distal portion 120 has a distal screw thread 124 provided thereon. Some bone screws can have multiple threads at the distal portion.

Between the threaded proximal and distal portions 130, 120 is a medial portion 110 that does not have any screw threads and is configured in a cylindrical shape with smooth finish. The threadless medial portion 110 keeps the threaded proximal and distal portions 130, 120 apart by a distance. The lengths of the proximal portion 130, the medial portion 110, and the distal portion 120 can be varied depending on the particular intended application for the bone screw 100. The bone screw 100 may also include a cannulation 140 extending longitudinally through the full length of the bone screw. At the distal end 122 of the distal portion 20, flutes 121 can be cut into the distal screw threads 124 to provide the distal end 122 with self-drilling configuration.

The proximal screw thread 134 may or may not have flutes or notches cut into it. In the illustrated example of bone screw 100, the proximal screw thread 134 is continuous and does not have any flutes or notches cut into it.

The particular structural details of the bone screw that may be used in combination with the washer described can vary depending on the particular bone screw selected for the application. Some examples of such structural details are the cross-sectional thread profiles and the pitch of the threads. The thickness of the threads at the crests of the threads are same.

The major diameter d1 of the distal threads 124 is substantially the same as the minor diameter d2 of the proximal thread 134. It should be noted that the major diameter d3 of the proximal thread 134 measured across from tip-to-tip of the proximal thread 134 is larger than the minor diameter d2.

In some bone screws, the proximal portion 130 is tapered with the minor diameter d2 and the major diameter of the proximal thread 134 increasing towards the proximal end 132. In such case, the major and minor diameters d3, d2, respectively, at the proximal portion 130 of the bone screw 100 will be fixed to be the diameters d3 and d2 measured at the distal end 131 of the proximal portion 130 for the purposes of discussing the bone screw's use in combination with the washers.

In any case, the bone screws for use in combination with the washers described herein is configured such that the diameter D3 of the leading end openings 17a, 27a of the washer embodiments 10, 20, respectively, is larger than the major diameter d1 of the distal threads of the bone screw but smaller than the major diameter d3 of the proximal thread 134. This allows the distal portion of the bone screw to freely pass through the central bore 15, 25 of the washers 10, 20 without any interference. However, because the major diameter d3 of the proximal thread 134 is larger than the diameter D3, the proximal portion of the bone screw will not fit through the leading end openings 17a, 27a.

Figure 10:
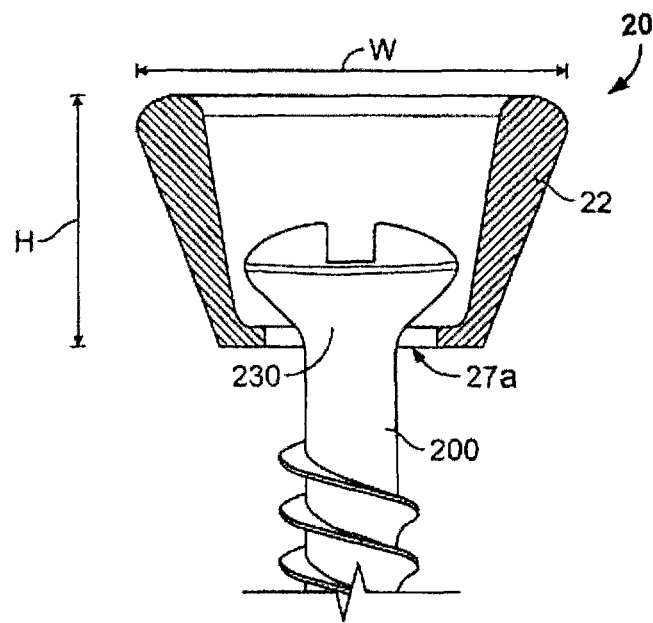
FIG. 10 is a perspective cross-sectional view of the washer embodiment of FIG. 6 shown in combination with a bone screw having a conventional non-threaded head.
Figure 13:
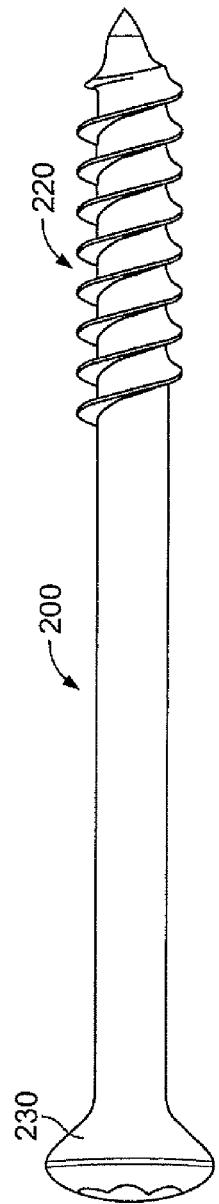
FIG. 13 is a plan view of another example of a bone screw that can be used in combination with the washers described herein.

FIG. 13 is a plan view of another example of a bone screw 200 that can be used in combination with the washers described herein. The bone screw 200 has a conventional non-threaded screw head 230 at the proximal end. As illustrated in FIGS. 5 and 10, the diameter of the screw head 230 is small enough to fit into the central bores 15, 25 of the washers 10, 20, respectively, but larger than the leading end openings 17a, 27a. The screw 200 has threaded distal portion 220 for engaging the distally positioned bone fragment.

Figure 14:
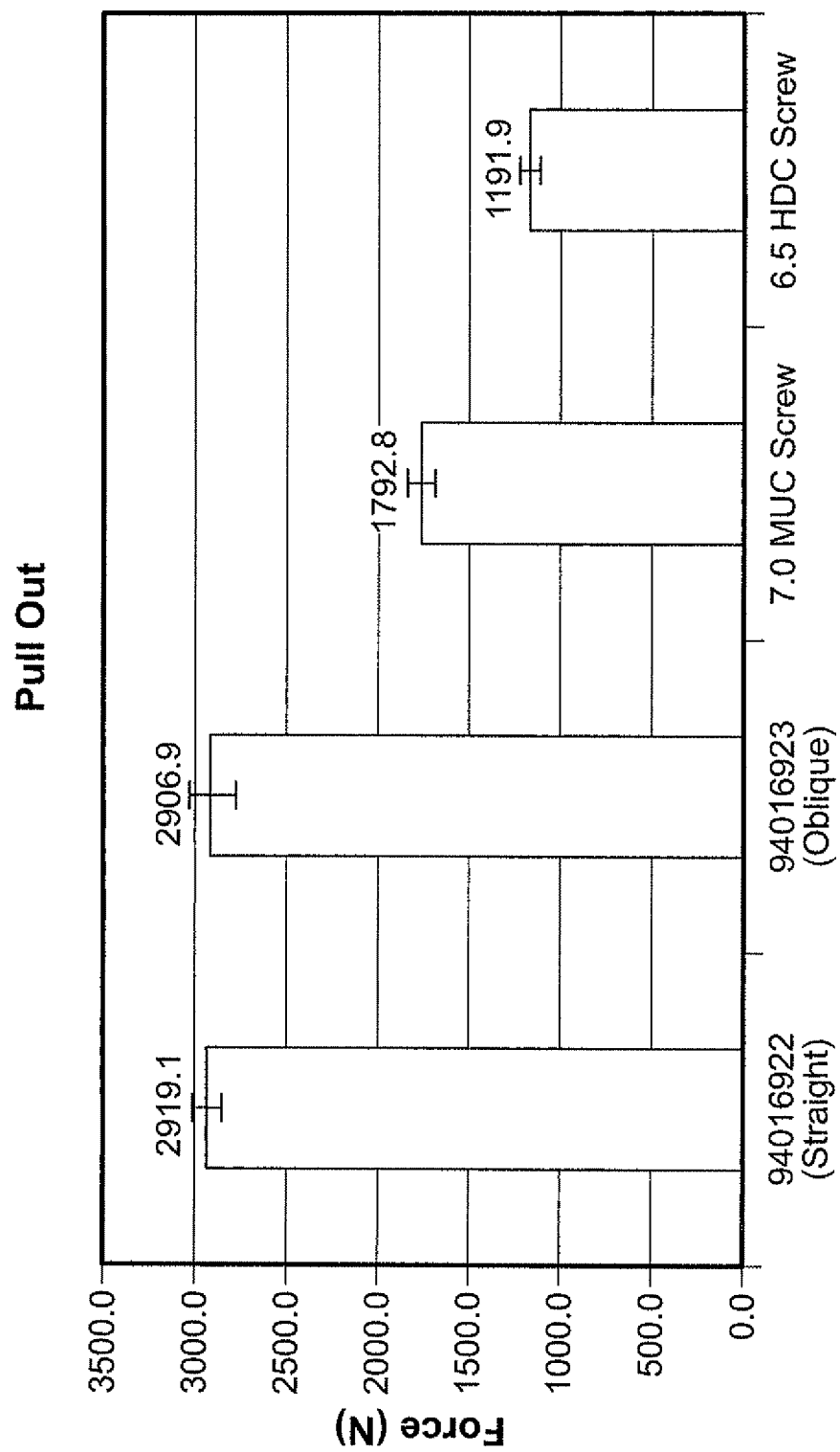
FIG. 14 is a proximal screw and washer pullout test results comparing the pullout force measured on two embodiments of the washer of the invention and proximal head pullout force of two screws without the use of the washer.

FIG. 14 shows a bar graph of the measured pull out force test results comparing the proximal end pull out force of a 7.0 MUC Screw (Wright Medical Technologies, Inc., Arlington, Tenn.) when using the two embodiments of the washers described herein against the proximal end pull out forces of 7.0 mm MUC Screw and 6.5 mm HDC Screw without the use of the washers. The pull out force measurements were conducted using polyurethane foam synthetic cancellous bone specimen blocks (e.g. Sawbones, Pacific Research Laboratories, Inc., Vashon, Wash.) of 20 lbs/ft$^3$ density. The straight and oblique washers tested had the following dimensions: 13 mm×6 mm. 13 mm being the outside diameter of the washers at the trailing end, marked as W in FIGS. 5 and 10. 6 mm being the length of the washers from the leading end to the trailing end, marked as H. The 7.0 mm MUC Screw had the following relevant dimensions for the threaded proximal end that was threaded into the Sawbone specimen: 10 mm×6 mm. The 6.5 mm HDC Screw had the following relevant dimensions for the threaded cap portion that was threaded into the Sawbone specimen. 9 mm×6 mm. The standard screws and the screw/washer combinations were driven into the synthetic bone specimen blocks and the screws were pulled out by an MTS machine and the pull out forces were recorded. As shown, both washer embodiments exhibited substantial improvements in the pull out forces as measured.

Depending the requirements of the particular application, the washer disclosed herein can be made with any variety of materials that are suitable and approved for implanting in human body. The washer can be made from surgical grade metals such as, for example, titanium, titanium alloys, ASTM-316L stainless steel Alternatively, the washer can be fabricated from bio-absorbable material. Such material would be useful in applications where additional surgical procedure to remove the washers is not desired and bone is permitted to form around the metallic screw as the bio-absorbable washer is absorbed by the patient's body. Such washer would also gradually reduce the compression on the bone fragments as the washer is absorbed. Other polymers such as highly purified polyhydroxyacids, poyamines, polyaminoacids, copolymers of amino acids and glutamic acid, etc. can be used also.

The use of the washer disclosed herein in conjunction with a compression bone screw allows proper seating of the threaded proximal portion of the bone screw even when the structural integrity of the bone at the proximal end is not in optimal condition to threadably engage the proximal portion of the bone screw. The washer also allows the proximal portion of the bone screw to countersink into the central bore of the washer under the surface of the bone avoiding any undesirable interference with joint articulation or soft tissue damage.

What is claimed is:

1. A washer for use with a compression bone screw in the reduction and fixation of bone fragments, the compression bone screw having a threaded proximal portion, said washer having a central axis and comprising:
   a frusto-conical body made of a metal having a leading end, a trailing end, an exterior surface that extends between the leading end and the trailing end and defining a frusto-conical surface that extends between the leading end and the trailing end and an interior surface;
   a central bore defined by the interior surface for insertion of the bone screw, the central bore extending between a first opening at the leading end and a second opening at the trailing end, the central bore having a first diameter at the leading end and a second diameter at the trailing end, and the interior surface being tapered, whereby the central bore's first diameter is larger than the second diameter; and
   an inwardly extending flange provided at the leading end that further reduces the central bore's opening at the leading end, wherein the exterior surface of the frusto-conical body has a greater taper angle than a taper angle of the interior surface, whereby the washer allows engagement of the threaded proximal portion of the compression bone screw with bone fragments where the bone fragments are structurally compromised.

2. The washer of claim 1, wherein the tapered interior surface has a taper angle of 4 to 8 degrees from the washer's central axis.

3. The washer of claim 1, wherein the tapered interior surface has a taper angle of 6 degrees from the washer's central axis.

4. The washer of claim 1, wherein the central bore's first opening has an interior perimeter and the flange provided at the leading end is an annular structure continuously extending along the central bore's first opening's interior perimeter.

5. The washer of claim 1, wherein the central bore's first opening has an interior perimeter and the flange provided at the leading end comprises at least two segments extending along the central bore's first opening's interior perimeter.

6. The washer of claim 1, wherein the taper angle of the exterior surface is at 20 degrees from the washer's central axis.

7. The washer of claim 1, wherein the taper angle of the exterior surface is at 15 degrees to 25 degrees from the washer's central axis.

8. The washer of claim 1, wherein the trailing end has a curved surface extending from the interior surface to the exterior surface of the frusto-conical body, the curved surface having a first curved surface between the interior surface and the trailing end, the first curved surface having a first radius of curvature and a second curved surface between the exterior surface and the trailing end, the second curved surface having a second radius of curvature, wherein the first radius of curvature is greater than the second radius of curvature.

9. The washer of claim 8, wherein the first radius of curvature is at least $50/1000$ inches.

10. The washer of claim 8, wherein the second radius of curvature is at least $20/1000$ inches.

* * * * *